US009132221B2

(12) United States Patent
Völker

(10) Patent No.: US 9,132,221 B2
(45) Date of Patent: Sep. 15, 2015

(54) COMBINATION OF A SINGLE-STATION REVERSE OSMOSIS DEVICE WITH A HEMODIALYSIS DEVICE

(76) Inventor: Manfred Völker, Blankenbach (DE)

( * ) Notice: Subject to any disclaimer, the term of this patent is extended or adjusted under 35 U.S.C. 154(b) by 660 days.

(21) Appl. No.: 13/468,236

(22) Filed: May 10, 2012

(65) Prior Publication Data
US 2013/0032518 A1 Feb. 7, 2013

(30) Foreign Application Priority Data
Aug. 1, 2011 (DE) .......................... 10 2011 109 093

(51) Int. Cl.
| A61M 1/36 | (2006.01) |
|---|---|
| C02F 1/36 | (2006.01) |
| C02F 1/44 | (2006.01) |
| C02F 1/48 | (2006.01) |
| B01D 61/02 | (2006.01) |
| B01D 61/10 | (2006.01) |
| B01D 61/12 | (2006.01) |
| B01D 61/58 | (2006.01) |
| B01D 63/02 | (2006.01) |
| B01D 65/02 | (2006.01) |
| A61M 1/16 | (2006.01) |
| B01D 61/24 | (2006.01) |
| C02F 1/467 | (2006.01) |
| C02F 103/02 | (2006.01) |

(52) U.S. Cl.
CPC .......... A61M 1/1656 (2013.01); B01D 61/025 (2013.01); B01D 61/10 (2013.01); B01D 61/12 (2013.01); B01D 61/58 (2013.01); B01D 65/02 (2013.01); B01D 65/022 (2013.01); B01D 65/027 (2013.01); C02F 1/441 (2013.01); B01D 61/243 (2013.01); B01D 63/02 (2013.01); B01D 2311/243 (2013.01); B01D 2313/50 (2013.01); B01D 2313/58 (2013.01); B01D 2321/22 (2013.01); B01D 2321/24 (2013.01); B01D 2321/34 (2013.01); B01D 2321/40 (2013.01); B01D 2325/48 (2013.01); C02F 1/36 (2013.01); C02F 1/44 (2013.01); C02F 1/4672 (2013.01); C02F 1/48 (2013.01); C02F 2103/026 (2013.01)

(58) Field of Classification Search
CPC ............ A61M 1/656; C01F 1/36; C01F 1/44; C02F 1/441; C02F 1/48; C02F 2103/026; B01D 61/025; B01D 61/10; B01D 61/12; B01D 61/58; B01D 61/243; B01D 63/02; B01D 65/02; B01D 65/022; B01D 65/027; B01D 2321/24; B01D 2321/22; B01D 2311/243; B01D 2321/40; B01D 2325/48
USPC ............... 210/191, 192, 195.2, 1, 198.1, 223, 210/205, 243, 251, 321.69
See application file for complete search history.

(56) References Cited

U.S. PATENT DOCUMENTS

| 4,784,771 A * | 11/1988 | Wathen et al. ............. 210/195.2 |
| 5,032,265 A * | 7/1991 | Jha et al. .................... 210/195.2 |
| 6,936,172 B2 * | 8/2005 | Hebert ....................... 210/195.2 |

FOREIGN PATENT DOCUMENTS

| DE | 20203733 U1 | 6/2002 |
| DE | 102009031043 A1 | 1/2011 |
| DE | 102009057562 A1 | 6/2011 |
| DE | 102010048616 A1 | 3/2012 |

* cited by examiner

Primary Examiner — David A Reifsnyder
(74) Attorney, Agent, or Firm — Greer, Burns & Crain, Ltd.

(57) ABSTRACT

A combination of a single-station reverse-osmosis (RO) device comprising a hemodialysis device (HD device) is characterized in that at least one cleaning chamber for the raw water and/or for the permeate is arranged, and that upon request by the HD device the permeate flows either via the water inlet valve into the HD device or via a flushing valve of the HD device to an outlet.

14 Claims, 2 Drawing Sheets

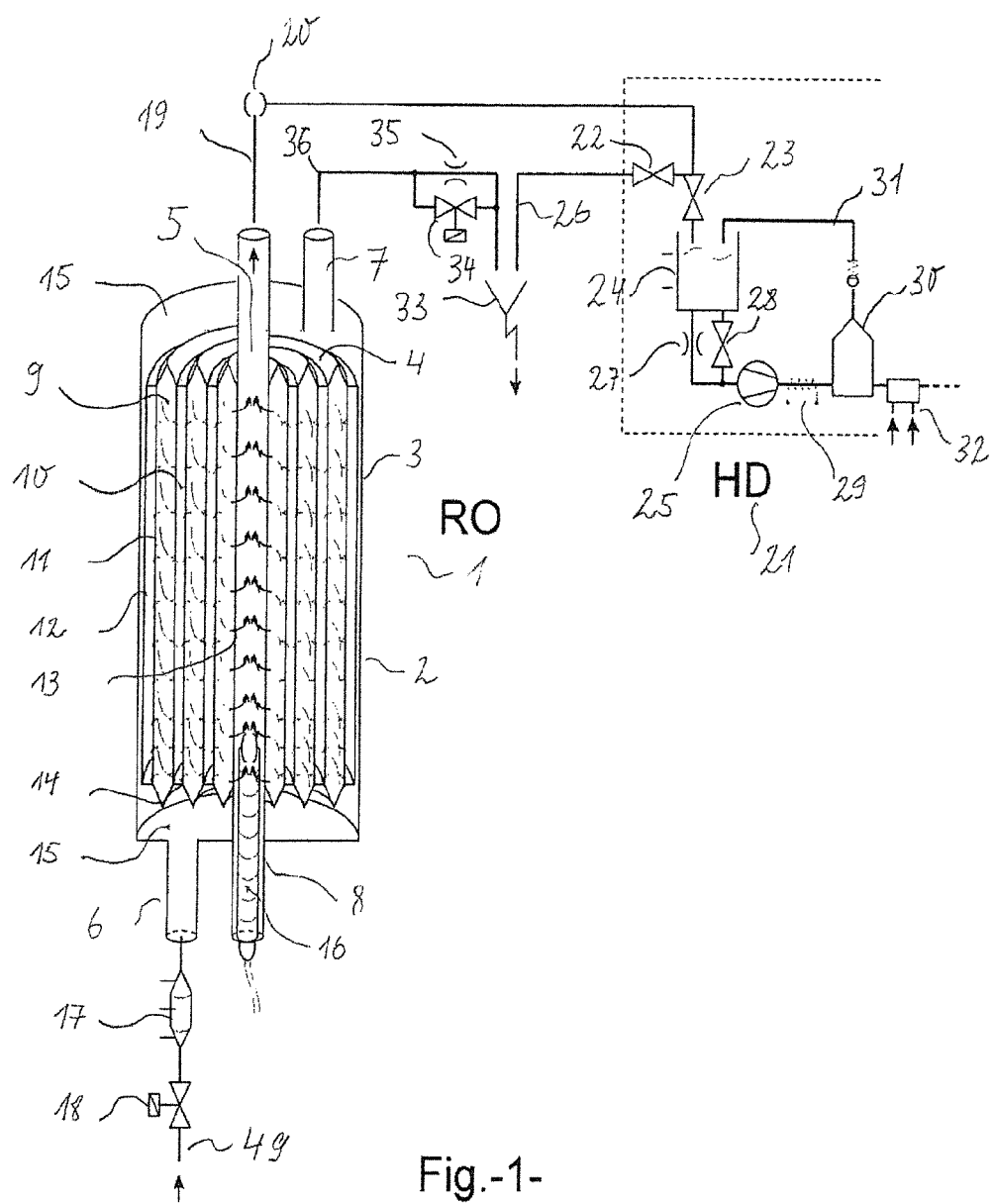
Fig.-1-

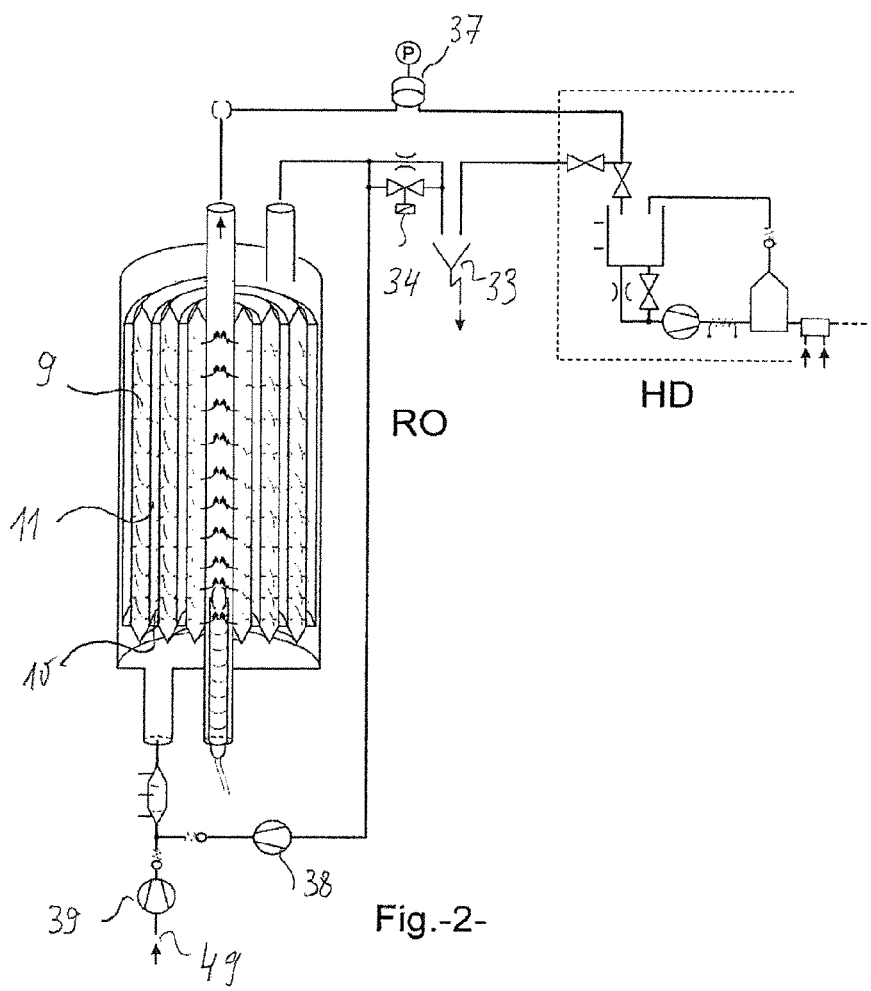
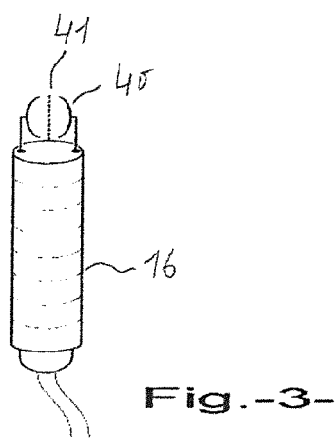
Fig.-3-
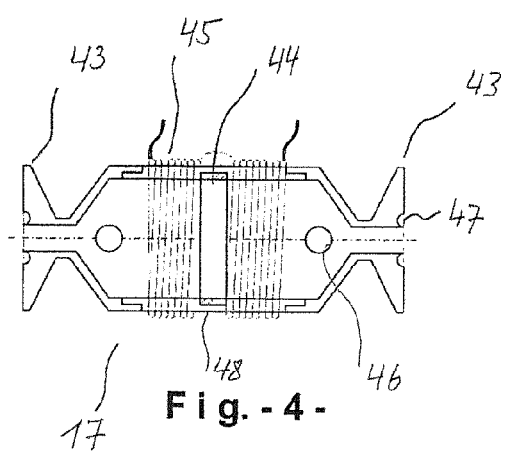
Fig.-4-

COMBINATION OF A SINGLE-STATION REVERSE OSMOSIS DEVICE WITH A HEMODIALYSIS DEVICE

FIELD OF THE INVENTION

It is the objective of this development to feed consumers, particularly hemodialysis devices, with high-purity permeate of a chemically and hygienically high quality at low costs while keeping the installation efforts as small as possible.

Further applications of this development for other fields, e.g. for laboratory or biology or also pharmacy technology, as a device for the preparation of high-purity flushing liquid, or also for the production of liquid for making medicaments, cell cultures or the like are conceivable and feasible.

BACKGROUND OF THE INVENTION

Especially in the hemodialysis field, central-supply reverse-osmosis systems are normally used with permeate supply lines that have to be installed in a correspondingly complicated way. Serious drawbacks of the central reverse-osmosis systems are on the one hand the high risk of non-treatment in the case of device failure and on the other hand the high installations costs and the difficult hygienic safety of the installation.

Single-station reverse-osmosis systems are mainly used for reasons of space in the intensive-care fields. For the chronic hemodialysis (HD), the supply of the dialysis devices with permeate by single-station reverse osmosis (RO) systems is not feasible at the moment for reasons of costs.

Further problems arising in the combination of RO system and HD device are posed by the missing evidence that the permeate supply device has no dead spaces for reasons of bacterial input into the HD device and can be disinfected completely.

To this end an integrated chemical or thermal disinfection of the distribution system, including the HD devices, is carried out according to the prior art.

Another serious flaw is the decreasing efficiency and service life of the reverse osmosis membrane due to irreversible deposits, the reason being that biomass and hardly soluble salts are often contained in the supply water for the RO system.

SUMMARY OF THE INVENTION

It is therefore the purpose and aim of the invention to ensure the permeate supply of a HD device with minimal technical efforts together with a constantly high membrane performance and the best microbiological quality.

This object is efficiently achieved in that the RO system preferably comprises a disposable, i.e. single-use, membrane and is equipped by taking only minimal technical efforts in such a manner that the full function will only be noticed upon coupling with the HD device in such a manner that on the one hand the permeate supply takes place in a chemically irreproachable way and without any dead space owing to the joint use of functional elements and that on the other hand it is possible due to the communication between HD device and RO system to use water and energy in a way that helps to save resources.

With great advantage, valves of the HD device are here used for the release or the flushing of the high-purity connection line.

The preventive disinfection of the high-purity connection line to the HD device takes a prominent position. To this end the invention advantageously provides a cleaning chamber in the permeate collection tube of the reverse osmosis membrane.

Advantageously, a cleaning chamber is also provided at the primary side of the reverse osmosis system.

The function of the cleaning chambers is on the one hand the decontamination of the microorganisms and on the other hand the stabilization of the hardeners, so that efficiency-reducing deposits on the reverse-osmosis membrane are prevented.

This is accomplished through the construction of the cleaning chamber which allows an electrical or magnetic or electromagnetic or electrolytic or sonographic effect or a combination of different physical effects of the liquid flowing therethrough. It has been detected in experiments that electrolysis takes place by means of a water irradiation frequency in the VHF range of preferably 13.56 MHz. This form of the cleaning chamber can also be used as a decontamination device.

Microorganisms are here either oxidized or they are prevented by electrical pulses from multiplying or their multiplication is diminished by said pulses.

The physical anti-lime function consists in the stabilization of the lime dissolved in the water in such a manner that the normally large water molecule clusters with their dipole-like electrical charge are broken up and arrange themselves such that predominantly very tiny water molecules clusters are formed that do not tend to precipitate or only show a minor tendency to precipitation.

The use and the place of installation of the cleaning chambers are however not limited to the described function.

Since the disinfection action of the electrolytically produced oxygen radicals as well as the stabilization of the lime crystals in the liquid are only temporary after the cleaning chamber has been switched off, the flow-resistance means of the RO system is advantageously opened periodically and/or at the end of an operating cycle by means of a bypass valve. This suddenly increases the flow in the primary circulation circuit and the surfaces of the liquid-conducting components are flooded and flushed.

To support the disinfecting action, the membrane collection tube or the membrane and spacer materials may be coated with anti-microbiocidal agents.

Since the action of the cleaning chamber cannot directly be detected by the user by way of its physical effect or its effects on crystal formation or contamination, a cleaning sensor may advantageously be provided for primary and secondary circuit.

Components or liquid-conducting lines may here be designed with transparent or translucent material to check the contamination visually or electro-electronically.

In an advantageous configuration the transmitter/receiver unit is arranged in one plane. The optical transmitter signal is here projected onto an opposite reflecting surface and is reflected from there to the optical receiver.

A further configuration of the contamination sensor is that the sensor determines the deposition of biological dirt layers in that this deposition reflects, by irradiation e.g. with UV light, a fluorescent, measurable response signal corresponding to the layer thickness.

With great advantage, in order to improve the impact in time and to enhance the physical cleaning effects, an additional circulation pump can be connected with a cleaning chamber between the concentrate outlet and the mixed water inlet. This may be an additional cleaning chamber with a different physical effect with respect to the cleaning chamber.

A flow through the primary circuit in the sense of an optimal overflowing of the membrane is here ensured, namely substantially independently of the action of the pump used for mixed-water supply, pressure build-up and circulation performance.

Owing to this invention both a controlled preventive avoidance of the biofilm in the primary circuit of the membrane and a cost-saving disinfection of the permeate supply without dead spaces are possible.

It is conceivable that the reverse-osmosis membrane indicated in this invention will soon be replaced—due to the rapid development of selective hollow-fiber membranes—by a combination which is similar to this invention and made up of HD device and upstream hollow fiber type softener/sterile filter membrane which can be produced at lower costs. The present invention will also cover this field on condition that the same process-technological tasks are concerned.

As is generally known, the functional principle of reverse osmosis systems consists in that the water to be treated is guided in a filter module under pressure along the surface of a semipermeable membrane, with part of the water, the so-called permeate, passing through the membrane and being collected at the other side of the membrane and supplied to the points of consumption. The part of the raw water that does not pass through the membrane and is enriched with retained substances, the so-called concentrate, flows at the end of the flow section of the primary circuit out of the membrane module.

In the case of selective hollow-fiber membranes, a filtration method is here also concerned in which specific substances in the water are retained to filter a liquid which can be used for the hemodialysis treatment. In this case the application of oxidizing disinfectants and the use of cleaning cells at the secondary side have to be slightly adapted with respect to material compatibility and design.

The following text describes the use of the RO membrane.

BRIEF DESCRIPTION OF THE DRAWINGS

FIG. 1 shows a combination of a reverse osmosis system with a hemodialysis device.

FIG. 2 shows a second embodiment of a combination reverse osmosis system with a hemodialysis device with an added buffer chamber.

FIG. 3 shows a cleaning cell for the permeate collection tube.

FIG. 4 shows a cleaning cell for the water supply line.

DETAILED DESCRIPTION OF THE PREFERRED EMBODIMENTS

The scheme in FIG. 1 represents the combination of a reverse osmosis (RO) system (1) with a hemodialysis device (HD device) (21) and the cooperation of joint functional elements.

The raw water to be treated flows out of the feeding line (49) via the valve (18) through a cleaning chamber (17) into the pressure tube (3) which is equipped with an RO membrane (4). The primary circuit of the RO membrane and of the water supply channels (10) is separated by the semipermeable membrane (11) from the secondary circuit (9) and the permeate pockets, respectively.

The permeate flows out of the permeate pockets (9) through the permeate collection tube perforations (13) via the permeate collection tube (5) and connection line (19) to the HD water or permeate inlet valve (23) of the HD device (21).

Flawed permeate produced in excess or measured by the conductivity cell (20) can flow at the end of the line (19) via an inserted HD flushing valve (22) with pressure-maintaining function to the outlet (33).

The pressure needed for filtration in the primary circuit of the RO filter (2) is produced with a flow-resistance means (35) which is inserted into the concentrate line (36) downstream of the RO filter, e.g. in the form of a throttle valve or a pressure-maintaining valve.

When permeate is requested by the HD device (21), the water inlet valve (18) opens, and after release by the LF cell (20) the HD device is fed via the HD water inlet valve (23).

In the case of an inadequate permeate quality or also in the case of necessary flushing programs, the HD water inlet valve (23) is closed and the flushing valve (22) of the HD device is opened, so that the unused permeate or the flushing liquid flows via the flushing line (26) to the outlet (33).

In the HD device 21 the introduced permeate is prepared via the degassing throttle (27), the pump (25) of the HD device, the heater (29) and the degassing chamber (30) for the HD treatment. The HD device includes a circulation line (31) and a concentrate and bicarbonate supply means (32).

The permeate collection tube (5) comprises an accommodating means (8) for a cleaning cell (16) the electrodes (40) of which output oxidants into the permeate, e.g. oxidants such as atomic and or elementary oxygen or ozone or OH hydroxyls or radio waves for producing oxidants.

The oxidant produced is passed together with the permeate through the line (19) and the flushing valve (22), which is first opened, to the outlet (33).

In order to reduce the flushing flow, the valve (22) can here be clocked. It is also possible to include an additional flow-resistance means (not shown).

Now shown is an impurity cell for detecting organic or inorganic deposits, both within the concentrate line (36) and in the permeate line (19).

To avoid deposits at the primary side of the membrane, i.e. on the inside of the pressure tube (3), the liquid channels (10) and the outflow line (36), the cleaning cell (17) can also be activated during the flushing and also the feeding process for the HD device 21.

Preferably, the flushing valve (34) is opened at cyclic flushing intervals and the whole primary circuit 10 has liquid flowing therethrough and is flushed.

The illustrated actuators and sensors can be controlled by the HD device and also by HD device and RO system in combination. The spatial arrangement of these functional elements as a part of the HD device is also possible.

FIG. 2 additionally shows a buffer chamber (37) which serves on the one hand the faster permeate supply into the HD device (21) and on the other hand the generation of a negative transmembrane pressure. When a negative transmembrane pressure is produced, the filtering direction is reversed by interrupting the water supply (49) and by opening the flushing valve (34). In this process, the permeate which is contained in the buffer vessel (37) flows back via the permeate pockets (9) to the primary side (10), thereby loosening the deposits positioned on the membrane surface (11). With the opening of the water supply means (49) these are washed away to the outlet (33).

Pump (39) raises the pressure in the primary circuit and thereby improves the filtering capacity.

The circulation pump (38) also enhances the performance, and especially contributes to the saving of water, in that the overflow at the primary side gets a greater proportion in relation to the permeate performance.

FIG. 3 schematically illustrates a cleaning cell with 2 electrodes (40) that can be introduced sealingly in form-fit fashion into the permeate collection tube as anode, cathode and cation exchanger membrane as electrolysis cell.

FIG. 4 shows by way of example the configuration of a cleaning cell (17) with 3 electrodes, the middle electrode (44) being isolated in space and electrically from the two outer electrodes (43).

It is possible by way of a material selection and by way of the electrical connection type to operate the cleaning chamber (17) as an electrolysis cell or as an electromagnetic cell or as a cell with electrode connections for current and voltage, also capacitively.

A pole of the electrical supply device is here preferably applied to the bridged outer electrodes (43), and the other pole is applied to the middle electrode (44).

During operation of the cleaning chamber (17) as the electrolysis cell the two outer electrodes (43) are the cathodes and the middle electrode (44) is the anode. When used as an electrolysis cell, it is advantageous for the achievement of a higher efficiency to separate anodes and cathode chamber by cation exchanger membranes. Due to the low permeability of this membrane the arrangement of anode, membrane, cathode has to be modified to achieve a configuration (not shown) which is advantageous from the viewpoint of fluid technology.

This electrolysis cell serves to produce oxygen radicals for the inactivation of the microorganisms or also serves to reduce limescale.

FIG. 4 shows the structure of a combined cleaning chamber (17) with 3 electrodes and a coil winding (45).

Decalcification is here carried out via the force lines of the coil-generated magnetic field in the liquid.

The use of Teflon-encapsulated ring magnets in the liquid or ring magnets outside the isolating piece (48) instead of the coil winding (45) is possible.

In addition to the illustrated representations, various pre-filtration and post-filtration components are possible, such as e.g. additional input filters, as carbon, ultra-filter, or also as safety filter—sterile filter as post-filter.

1. Reverse osmosis (RO)
2. RO filter
3. Pressure tube
4. RO membrane
5. Permeate collection tube
6. Connection: water supply/pressure tube
7. Connection: concentrate
8. Permeate collection tube: accommodation means cleaning cell
9. Secondary side/permeate pockets
10. Primary circuit/side/water supply channels
11. Membrane
12. Outer membrane jacket
13. Permeate collection tube - perforations
14. Permeate pocket gluing
15. Pressure tube termination
16. Cleaning cell: permeate
17. Cleaning cell: water supply
18. Water inlet valve
19. Connection line HD device (permeate line)
20. Conductivity cell (LF cell)
21. Hemodialysis device (HD device)
22. HD flushing valve
23. HD water inlet valve
24. HD water inlet container with float or level sensors
25. HD pump
26. HD flushing line
27. Degassing throttle
28. Degassing bypass valve
29. HD heater
30. Degassing chamber
31. HD circulation line
32. Concentrate/bicarbonate supply
33. Outlet
34. Flushing valve
35. Flow resistance
36. Concentrate line
37. Buffer chamber
38. Circulation pump
39. Pressure raising pump
40. Electrodes
41. Membrane
42. Combination cleaning cell
43. Outer electrodes
44. Inner electrode
45. Coil winding
46. Ultrasound
47. Accommodation sealing ring
48. Insulation tube
49. Feed line

The invention claimed is:

1. A combination comprising a single-station reverse osmosis device (RO device) with a hemodialysis device (HD device), the RO device comprising a filter with a membrane which separates a primary circuit from a secondary circuit, a raw-water supply line terminating in the primary circuit and the secondary circuit being connected to a permeate inlet valve of the HD device via a connection line containing a conductivity measuring device, and a concentrate connection of the primary circuit leading to an outlet via a concentrate line containing a flow-resistance means, wherein at least one cleaning chamber for at least one of the raw water and the permeate is connected to the RO device, and that upon request by the HD device, the permeate flows either via the permeate inlet valve into the HD device or via a flushing valve of the HD device to the outlet.

2. The combination according to claim 1, wherein the secondary circuit comprises a permeate collection tube.

3. The combination according to claim 2, wherein said at least one cleaning chamber comprises a permeate cleaning chamber in the permeate collection tube.

4. The combination according to claim 3, wherein the permeate cleaning chamber is installed into an end section of the permeate collection tube facing away from the connection line.

5. The combination according to claim 1, wherein said at least one cleaning chamber comprises a water supply cleaning chamber inserted into the raw-water supply line.

6. The combination according to claim 1, wherein the at least one cleaning chamber includes oxidants for fighting microorganisms.

7. The combination according to claim 6 wherein the at least one cleaning chamber includes at least one of electrical, magnetic, electromagnetic, electrolytic, and sonographic means on the liquid flowing therethrough.

8. The combination according to claim 1, wherein the at least one cleaning chamber includes agents for stabilizing lime crystals dissolved in water.

9. The combination according to claim 8 wherein the at least one cleaning chamber includes at least one of electrical, magnetic, electromagnetic, electrolytic, and sonographic means on the liquid flowing therethrough.

10. The combination according to claim 1, wherein a recirculation line provided with a pump connects the concentrate line upstream of the flow-resistance means to the raw-water feed line upstream of the at least one cleaning chamber.

11. The combination according to claim 1, wherein the connection line is provided with a permeate buffer chamber.

12. The combination according to claim 1, wherein the flushing valve is configured such that the flushing valve can open the flow-resistance means.

13. The combination according to claim 1, wherein the membrane is an exchangeable disposable membrane.

14. The combination according to claim 1, wherein said at least one cleaning chamber comprises a permeate cleaning chamber in a permeate collection tube, and a water supply cleaning chamber inserted into the raw-water supply line.

* * * * *